US008603948B2

(12) United States Patent
Chaganti et al.

(10) Patent No.: US 8,603,948 B2
(45) Date of Patent: Dec. 10, 2013

(54) PANEL FOR THE DETECTION AND DIFFERENTIATION OF RENAL CORTICAL NEOPLASMS

(75) Inventors: Raju S. K. Chaganti, Hillsdale, NJ (US); Jane Houldsworth, Franklin Lakes, NJ (US)

(73) Assignee: Cancer Genetics, Inc., Rutherford, NJ (US)

( * ) Notice: Subject to any disclaimer, the term of this patent is extended or adjusted under 35 U.S.C. 154(b) by 0 days.

(21) Appl. No.: 11/932,422

(22) Filed: Oct. 31, 2007

(65) Prior Publication Data
US 2009/0111704 A1 Apr. 30, 2009

(51) Int. Cl.
*C40B 30/04* (2006.01)
(52) U.S. Cl.
USPC .......................................................... 506/16
(58) Field of Classification Search
None
See application file for complete search history.

(56) References Cited

U.S. PATENT DOCUMENTS

2005/0130193 A1    6/2005    Luxon et al.

OTHER PUBLICATIONS

Morita (Nov. 1991) Cancer Research vol. 51 p. 5817-5820.*
Altinok (Mar. 8, 2005) Pediatric and Developmental Pathology vol. 8 p. 168-180.*
Cremer et al. (1986) Human Genetics vol. 74 pp. 346 to 352.*
Andersson, et al., "Frequent gain of the human telomerase gene TERC at 3q26 in cervical adenocarcinomas," *British Journal of Cancer*, 2006, vol. 95, pp. 331-338.
Barocas, et al., Renal cell carcinoma sub-typing by histopathology and fluorescence in situ hybridization on a needle-biopsy specimen, *BJU International*, 2006, vol. 99(2), pp. 290-295.
Brauch, H. et al., Genetic alterations in sporadic renal-cell carcinoma: molecular analyses of tumor suppressor gene harboring chromosomal regions 3p, 5q, and 17p, *World Journal of Urology*, 1994, vol. 12(3), pp. 162-168.
Carpenter, et al., "Molecular Cytogenetics," *Seminars in Pediatric Neurology*, 2001, vol. 8(3), pp. 135-146.
Clifford, Steven C., et al., "Inactivation of the von Hippel-Lindau (VHL) Tumour Suppressor Gene and Allelic Losses at Chromosome Arm 3p in Primary Renal Cell Carcinoma: Evidence for a VH1-Indendent Pathway in Clear Cell Renal Tumourigenesis," *Genes Chromosomes and Cancer*, 1998, vol. 22(3), pp. 200-209.
Heselmeyer, et al., "Gain of chromosome 3q defines the translation from severe dysplasia to invasive carcinoma of the uterine cervix," *Proc. Natl. Acad. Sci.*, 1996, vol. 93, pp. 479-484.
Heselmeyer, et al., "Advanced-Stage Cervical Carcinomas Are Defined by a Recurrent Pattern of Chromosomal Aberrations Revealing High Genetic Instability and a Consistent Gain of Chromosome Arm 3q," *Genes, Chromosomes & Cancer*, 1997, vol. 19, pp. 233-240.
Heselmeyer-Haddad, et al, Detection of Genomic Amplification of the Human Telomerase Gene (*TERC*) in Cytologic Specimens as a Genetic Test for the Diagnosis of Cervical Dysplasia, *American Journal of Pathology*, 2003, vol. 163(4), pp. 1405-1416.

(Continued)

*Primary Examiner* — Heather Calamita
*Assistant Examiner* — Christian Boesen
(74) *Attorney, Agent, or Firm* — Alston & Bird LLP

(57) ABSTRACT

The present invention provides a novel, highly sensitive and specific probe panel which detects the type of renal cortical neoplasm present in a biopsy sample. As such, the invention permits diagnosis of the predominant subtypes of renal cortical neoplasms without the use of invasive methods. The present invention further provides a molecular cytogenetic method for detecting and analyzing the type of renal cortical neoplasm present in a renal biopsy sample.

4 Claims, 4 Drawing Sheets

Representative FISH image of an Xp11 translocation-associated RCC showing break-apart of the Xp11 probe signal.

(56) References Cited

OTHER PUBLICATIONS

Heselmeyer-Haddad, et al., "Genomic Amplification of the Human Telomerase Gene (Terc) in Pap Smears Predicts the Development of Cervical Cancer," *American Journal of Pathology*, 2005, vol. 166(4), pp. 1229-1238.

Hughson, et al., "Clear-Cell and Papillary Carcinoma of the Kidney: An Analysis of Chromosome 3, 7, and 17 Abnormalities by Microsatellite Amplification, Cytogenetics, and Fluorescence In Situ Hybridization," *Cancer Genet Cytogenet*, 1998, vol. 106, pp. 93-104.

Jones, et al., "*Application of Molecular Diagnostic Techniques to Renal Epithelial Neoplasms*," Clin Lab Med, 2005, vol. 25, pp. 279-303.

Kaelin, Jr., William G., "The von Hippel-Lindau Tumor Suppressor Protein and Clear Cell Renal Carcinoma," *Clin Cancer Res*, 2007, vol. 13(2 Suppl), pp. 680s-684s.

Knight, et al., "Prognostic factors in localized renal cell cancer," *BJU International*, 2007, vol. 99(5), pp. 1212-1216.

Kovacs, et al., "Molecular Cytogenetics of Renal Cell Tumors," *Advances In Cancer Research*, 1993, vol. 62, pp. 89-124.

Paner, et al., "High Incidence of Chromosome 1 Abnormalities in a Series of 27 Renal Oncocytomas," *Arch Pathol Lab Med*, 2007, vol. 131, pp. 81-85.

Patel, et al., "Cytogenics and cancer," *Curr Opin Oncol*, 2000, vol. 12(1), pp. 62-67.

Rao, et al., "Chromosomal amplifications, 3q gain and deletions of 2q33-q37 are the frequent genetic changes in cervical carcinoma," *BMC Cancer*, 2004, vol. 4, pp. 1-9.

Sanjmyatav, et al., "Identification of Tumor Entities of Renal Cell Carcinoma Using Interphase Fluorescence In Situ Hybridization," *The Journal of Urology*, 2005, vol. 174, pp. 731-735.

Speicher, et al., "Specific Loss of Chromosomes 1, 2, 6, 10, 13, 17, and 21 in Chromophobe Renal Cell Carcinomas Revealed by Comparative Genomic Hybridization," *American Journal of Pathology*, 1994, vol. 145(2), pp. 356-364.

Stoltzfus, et al., Gain of chromosome 3q is an early and consistent genetic aberration in carcinomas of the vulva, *Int J Gynecol Cancer*, 2005, vol. 15, pp. 120-126.

Thrash-Bingham, Catherine A., et al., "Genomic Alterations and Instabilities in Renal Cell Carcinomas and Their Relationship to Tumor Pathology," *Cancer Research*, 1995, vol. 55(24), pp. 6189-6195.

Van Den Berg, et al., "Involvement of Multiple Loci on Chromosome 3 in Renal Cell Cancer Development," *Genes, Chromosomes & Cancer*, vol. 19, 99. 59-76.

Visakorpi, et al., "Sensitive Detection of Chromosome Number Aberrations in Prostate Cancer by Fluorescence In Situ Hybridization," *American Journal of Pathology*, 1994, vol. 145(3), pp. 624-630.

Wilhelm, et al., "Array-based Comparative Genomic Hybridization for the Differential Diagnosis of Renal Cell Cancer," *Cancer Research*, 2002, vol. 62, pp. 957-960.

Yokoi, et al., "*TERC* Identified as a Probable Target within the 3q26 Amplicon That Is Detected Frequently in Non-Small Cell Lung Cancers," *Clinical Cancer Research*, 2003, vol. 9, pp. 4705-4713.

Banks, et al., "Genetic and Epigenetic Analysis of von Hippel-Lindau (VHL) Gene Alterations and Relationship with Clinical Variablesin Sporadic Renal Cancer," *Cancer Res*, 2006, vol. 66(4), pp. 2000-2011.

Füzesi, et al., "Losses of 1p and chromosome 14 in renal oncocytomas," *Cancer Genetics and Cytogenetics*, 2005, vol. 160, pp. 120-125.

Höglund, et al., "Dissecting karyotypic patterns in renal cell carcinoma: an analysis of the accumulated cytogenetic data," *Cancer Genetics and Cytogenetics*, 2004, vol. 153, pp. 1-9.

Pérot, et al., "Five new cases of juvenile renal cell carcinoma with translocations involving Xp11.2: a cytogenic and morphologic study," *Cancer Genetics and Cytogenetics*, 2003, vol. 143, pp. 93-99.

Receveur, et al., "Characterization of quantitative chromosomal abnormalities in renal cell carcinomas by interphase four-color fluorescence in situ hybridization," *Cancer Genetics and Cytogenetics*, 2005, vol. 158, pp. 110-118.

Shuch, et al., "Prognostic Factors in Renal Cell Carcinoma," *Semin Oncol*, 2006, vol. 33(5), pp. 563-575.

Van Den Berg, et al., "Cytogenic Classification of Renal Cell Cancer," *Cancer Genet Cytogenet*, 1997, vol. 95, pp. 103-107.

\* cited by examiner

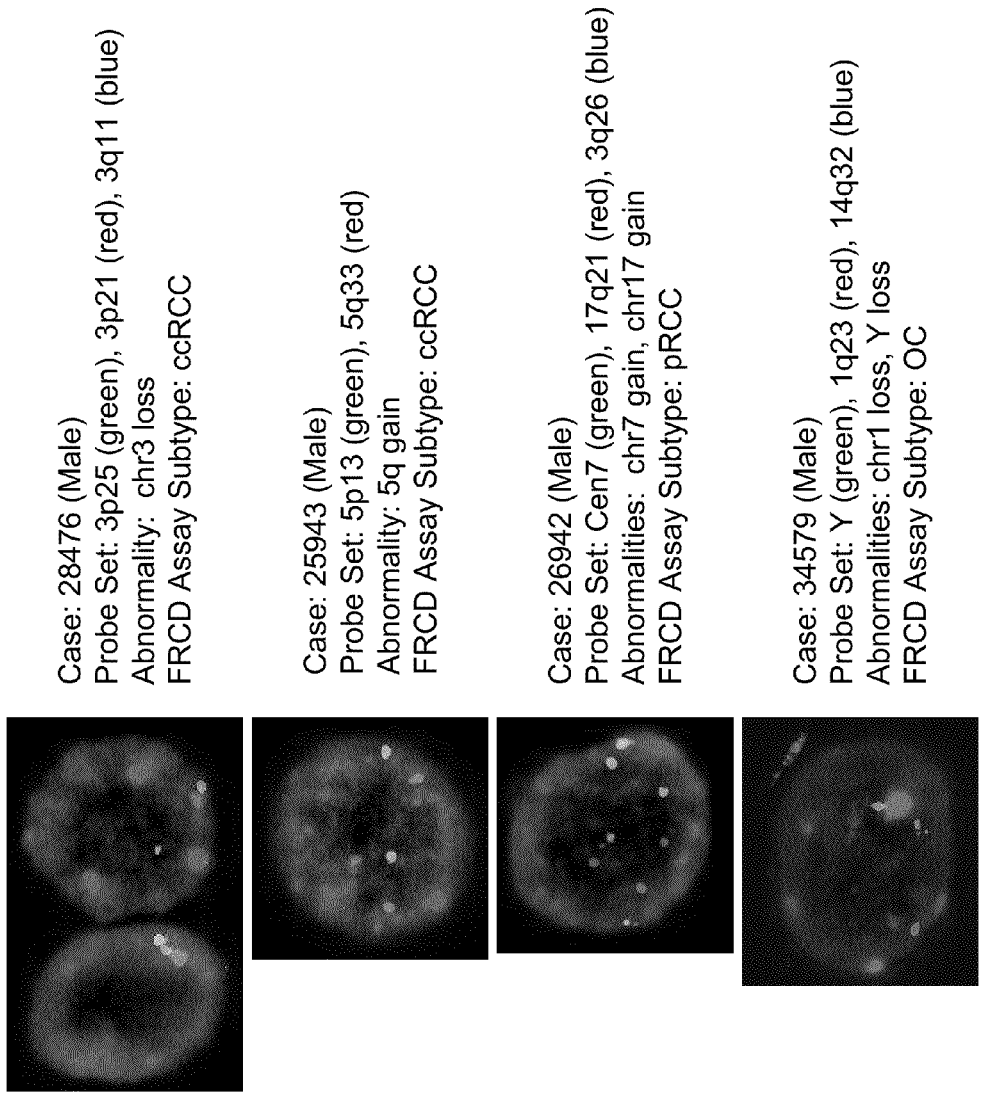
Figure 1. Representative images of chromosomal abnormalities as detected by the FRCD assay in renal mass needle biopsies.

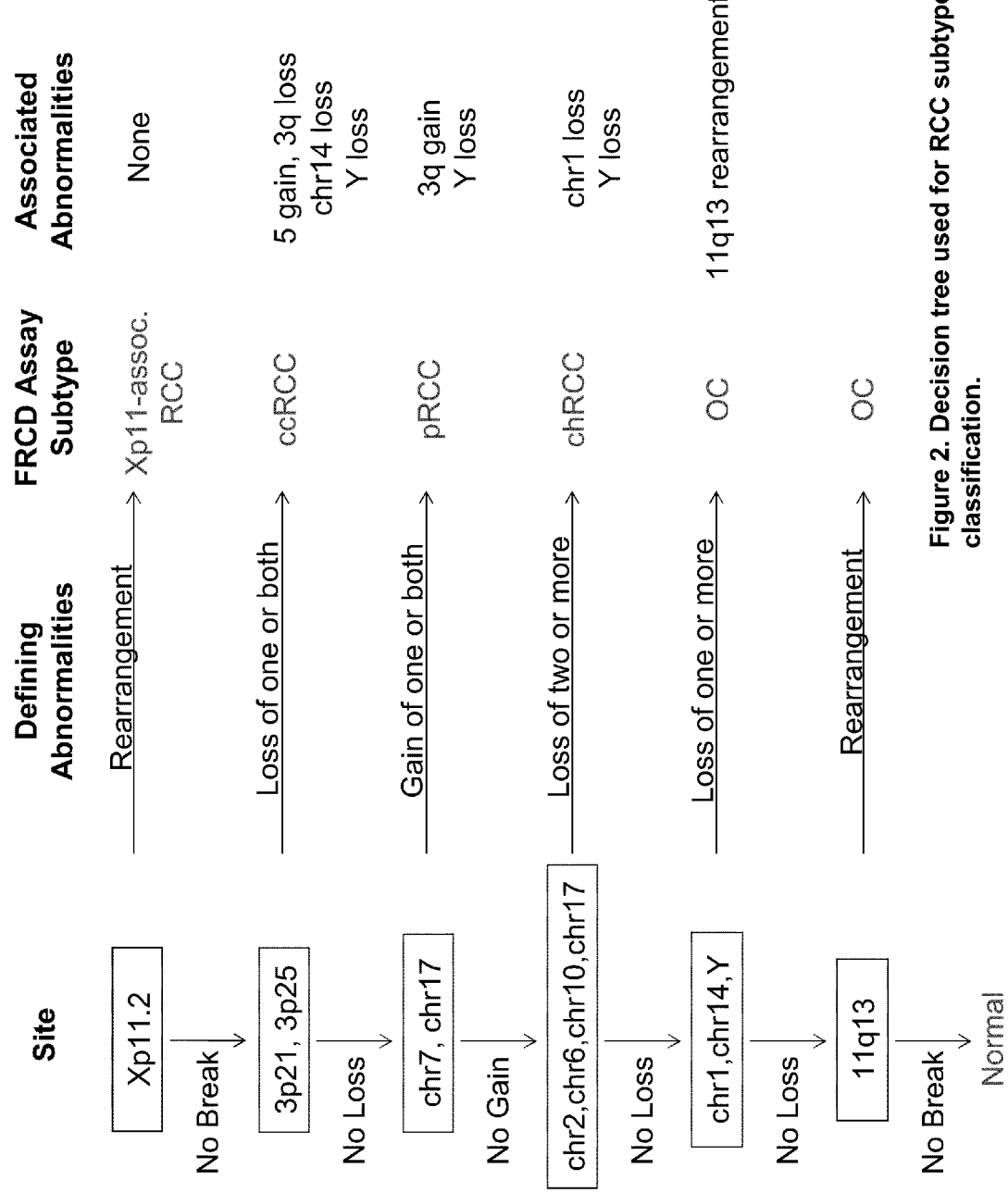
Figure 2. Decision tree used for RCC subtype classification.

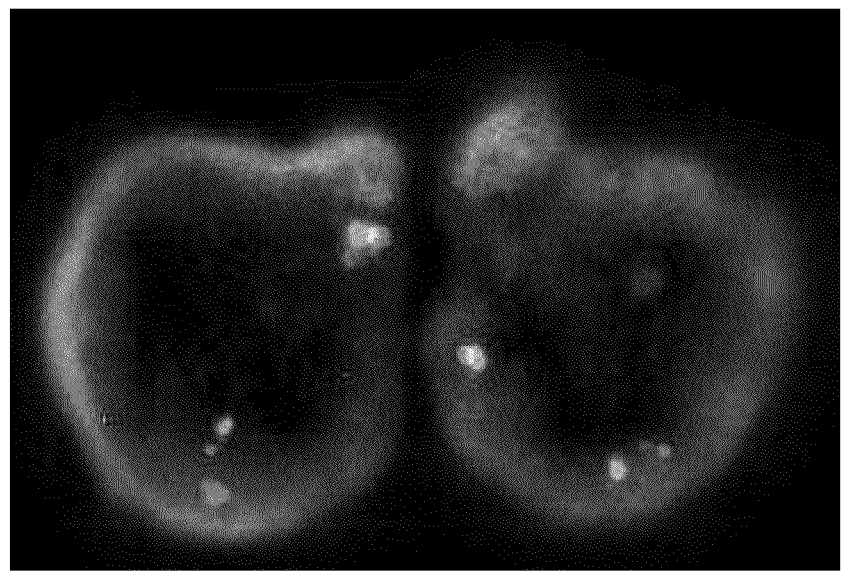
Figure 3. Representative FISH image of an Xp11 translocation-associated RCC showing break-apart of the Xp11 probe signal.

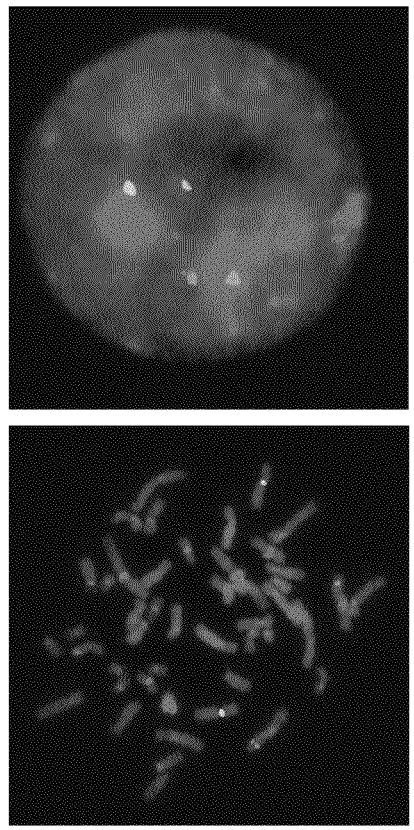
Figure 4. Representative hybridization signals of a single-copy probe set for 3q26 hybridized to normal lymphocyte spreads in the absence of Cot-1 DNA. Left: metaphase cell. Right: interphase cell. Red signal: single-copy 3q26 probe. Green signal: 7 Cen probe.

PANEL FOR THE DETECTION AND DIFFERENTIATION OF RENAL CORTICAL NEOPLASMS

The present invention provides a novel, highly sensitive and specific probe panel which detects the type of renal cortical neoplasm present in a biopsy sample. As such, the invention permits diagnosis of the predominant subtypes of renal cortical neoplasms without the use of invasive methods. The present invention further provides a molecular cytogenetic method for detecting and analyzing the type of renal cortical neoplasm present in a renal biopsy sample.

Throughout this application, various publications are referenced. Full citations for these publications may be found immediately preceding the claims. The disclosures of these publications are hereby incorporated by reference into this application in order to more fully describe the state of the art as of the date of the invention described and claimed herein.

BACKGROUND OF THE INVENTION

An increase in the use of state-of-the-art imaging techniques has led to the discovery of a greater number of small, incidentally discovered renal masses, benign and malignant. Up until now, current interventions in obtaining samples of the renal masses were limited to minimally invasive (e.g. needle biopsy) to standard surgical procedures. Currently, diagnosis of such masses for treatment decision making is limited to tests that rely on morphological analyses alone. However, such tests pose certain drawbacks. Two main limitations include: (i) the inability to obtain diagnostic material from minimally invasive procedures (e.g. needle biopsy) of adequate quantity and quality for morphological examination; and (ii) the inability to distinguish the predominant subtypes of renal cortical neoplasms morphologically.

Furthermore, a large proportion of patients with small, incidentally discovered renal masses are within an older, more frail population and for renal cell carcinoma (RCC), 60-70% of patients are asymptomatic. Thus, for patients with such masses, an alternative to invasive diagnostic methods, i.e., surgery, is required.

As such, there exists a need for a highly sensitive and specific molecular diagnostic method which does not require the use of surgery, and thus, does not require: (i) a large quantity of diagnostic material; and (ii) the use of standard pathological methods for classification and analysis. Indeed, applications, such as the present invention, that use samples obtained through minimally invasive procedures (e.g. needle biopsy) in order to detect and analyze changes on a molecular level are more likely to provide early detection than applications that rely on morphological analyses alone. And early detection of a specific disease state can greatly improve a patient's chance for survival by permitting early diagnosis and early treatment while the disease is still localized and its pathologic effects limited anatomically and physiologically.

Two key evaluative measures of any test or disease detection method are its sensitivity and specificity, which measure how well the test performs to accurately detect all affected individuals without exception, and without falsely including individuals who do not have the target disease. Historically, many diagnostic tests have been criticized due to poor sensitivity and specificity.

As such, this patent application describes an innovative, sensitive and specific molecular cytogenetic method-based detection test that is based on the inherent differential genetics of renal cortical neoplasms, and not on cell morphology.

The statistics with respect to kidney cancer in the United States are startling. In fact, in 2007, 51,190 Americans are expected to be diagnosed with kidney cancer and 12,890 are expected to die of the disease. Of these patients, 62% are male and 38% female. Overall, this represents approximately 3% of all cancers in the United States and comparatively the 7th most prevalent cancer in men and 8th in women (1).

Of all kidney cancers, renal cell carcinoma (RCC), arising in the cortex of the kidney, is the most common (90%), and is also the most lethal. The incidence of RCC has increased for the past 65 years by about 2% every year. The underlying cause for this is currently unknown. The median age at diagnosis of RCC is 65 years. Several risk factors for the disease have been identified and include both lifestyle (smoking and obesity) and hereditary factors. The most common hereditary type is that associated with von Hippel-Lindau disease (VHL), arising due to mutations in the VHL gene and is more often associated with young patients.

RCC is usually indicated as a suspicious mass involving the kidney that appears in a radiographic analysis such as a computed tomographic (CT) scan or in some cases ultrasound. In most cases, the scan is either performed in response to a symptomatic renal mass or for some other condition that incidentally lead to the detection of the lesion.

Following detection of a renal mass, an initial work-up is performed, including a thorough physical examination and a laboratory examination (complete blood cell count, comprehensive metabolic panel, coagulation profile, and urine analysis). Oftentimes, additional imaging analyses are necessary, including CT of the abdomen and pelvis (with and without contrast), and chest radiograph or CT scan of the chest or brain. In selected cases, an MRI may be used to determine vascular involvement of the inferior vena cava or the presence of brain metastases.

Next, depending on the clinical indications, recommendations for surgery or alternative therapies are provided. In the case of surgery, an understanding of the true pathology will not be obtained until several days after surgical resection. Needle biopsy is occasionally performed in the pre-treatment setting in those cases where risks of competing malignancies may exist, when a benign process is suspected, or prior to ablation procedures.

Historically, biopsy procedures for renal masses have been under-utilized due to prior studies showing diagnostic inaccuracy in using these small specimens for morphologic analysis. Although, as detailed below, more recent studies have indicated that preoperative renal biopsies play an important role in the clinical management of patients with radiological evidence for a renal mass. Thus, resulting in a need for the present invention.

It is also evident that using morphologic criteria alone to interpret biopsies is frequently "non-diagnostic" or can result in ambiguous interpretations due to the heterogeneous nature of these tumors. Thus, in an effort to overcome these issues, the present invention teaches that the biopsy specimen should be analyzed for the presence/absence of histologic subtype-specific genetic abnormalities to not only aid in differential diagnosis but also to improve the efficacy of preoperative biopsy.

The accurate identification of renal masses is of critical importance in all phases of clinical management of this disease. For patients with small lesions, an accurate diagnosis, which distinguishes between a benign and malignant lesion, would thus lead to the appropriate type of therapy. Thus, avoiding needless procedures being used on patients with benign lesions.

For patients with larger neoplasms, diagnosis of tumor subtypes would serve to stratify patients for their risks of local or regionally advanced disease that can be factored in to treatment selection recommendations (i.e., extent of surgical intervention, less invasive options or ablation).

In patients with metastatic disease, drug trials are currently based on post-surgical tumor diagnosis, causing 4-6 weeks in delay to potentially curative treatment while risking associated peri-operative complications, functional nephron loss, and convalescence-related quality of life changed for uncertain clinical benefit.

As defined herein, renal cortical neoplasms are tumors or other abnormal growths that arise from the cells of the renal parenchyma (the tissue that constitutes the essential or functional part of the kidney).

These neoplasms are morphologically classified as shown in FIG. 1. Both benign and malignant lesions are shown in FIG. 1 with the most common benign lesion, oncocytoma (OC), constituting 6-9% of renal cortical neoplasms. Of the malignant lesions, the most common subtype is clear cell RCC (ccRCC), followed by papillary RCC (pRCC), and chromophobe RCC (chRCC).

The identification of cytogenetic abnormalities consistently associated with the subtypes of renal cortical neoplasms have allowed the classification of RCC more precisely (FIG. 1) (3-11). The probe panel of the present invention was designed to take into account the single abnormalities that define a subtype, along with the secondary and complex abnormalities that together allow a more precise classification. These abnormalities also provide molecular clues to the underlying genetic basis of the disease. This is exemplified by the consistent loss of 3p25 in ccRCC which along with mutation analysis has indicated a role for the VHL locus even in sporadic ccRCC (12, 13).

Prior to applicants' invention, there were no probes which could accurately detect the type of renal cortical neoplasm present in a renal biopsy sample. Moreover, applicants' invention does not require large quantities of diagnostic material since the claimed probes are highly sensitive.

Thus, for the first time, accurate detection and analysis of the type of renal cortical neoplasm may be performed on a biopsy sample obtained using non-invasive methods.

As noted above, the present invention is directed to a novel molecular cytogenetic method-based probe panel which detects the type of renal cortical neoplasm present in a renal biopsy sample. As such, the invention permits diagnosis of the four predominant subtypes of renal cortical neoplasms without surgery.

SUMMARY OF THE INVENTION

This invention provides a panel for detecting the type of renal cortical neoplasm present in a sample, wherein said panel comprises a plurality of probes each of which is individually capable of hybridizing selectively to a specific marker or a correlate thereof associated with a chromosomal abnormality diagnostic or indicative of the type of renal cortical neoplasm.

This invention further provides a method for detecting the subtype of renal cortical neoplasm present in a sample, the method comprising: (a) a panel comprising a plurality of probes each of which is individually capable of hybridizing selectively to a specific marker or a correlate thereof associated with a chromosomal abnormality diagnostic or indicative of the subtype of renal cortical neoplasm; (b) hybridizing said sample with said plurality of probes; (c) analyzing the hybridization pattern of each of the said probes to said specific markers or correlates thereof after said hybridization, in order to detect the presence or absence of one or more chromosomal abnormalities associated with a subtype of renal cortical neoplasm; and (d) if one or more chromosomal abnormalities are detected within said sample, classifying the subtype of renal cortical neoplasm present according to the diagnosis matrix shown in FIG. 4.

BRIEF DESCRIPTION OF THE DRAWINGS

FIG. 1 A table classification of the predominant subtypes of renal cortical neoplasms and their frequently associated cytogenetic abnormalities.

FIG. 2 A table detailing the genomic abnormalities to be evaluated by FISH in renal masses to detect the type of renal cortical neoplasm present in such masses. The table consists of an identification of the predominant histologic subtypes of renal cortical neoplasms, their associated chromosomal abnormalities, the genetic locus of those abnormalities, a selection of correlate markers that map to the respective genomic regions and the respective fluorescent signals expected from differential probe labeling.

FIG. 3 In the routine development of any probe to be utilized in a clinical FISH-based assay, labeled probes are initially hybridized to normal peripheral blood lymphocyte preparations which include both interphase and metaphase cells. The reasons for this are the following: (i) to confirm the expected chromosome hybridization localization, (ii) to rule out chimerism, and, (iii) to establish the cut-offs for the presence/absence of the abnormality. FIG. 3 is a table detailing the cut-offs for the presence/absence of the chromosomal abnormality for each combination of the BAC-based probes. Specifically, the table lists the predominant histologic subtypes of renal cortical neoplams, their associated chromosomal abnormalities, the selected correlate markers, the respective results obtained upon hybridization to normal lymphocytes, and the signal pattern cut-offs (mean plus three standard deviations) above which for probes used in copy number evaluation would be considered to have an altered copy number.

FIG. 4 A diagnosis matrix or decision tree used for the classification of the subtypes of renal cortical neoplams. This diagnosis matrix allows for classification of renal biopsy sample based on the sequential loss/gain/rearrangement of the relevant genomic sites. Use of the diagnosis matrix in the manner shown in FIG. 4, allows one to analyze and interpret the chromosomal abnormalities detected by FISH and assign the corresponding subtype of renal cortical neoplasm to the renal biopsy sample.

DETAILED DESCRIPTION OF THE INVENTION

Introduction

The present invention provides a panel of highly sensitive and specific probes designed to detect the type of renal cortical neoplasm present in a sample. As such, the invention also provides a method for detecting a disease state and for discriminating between certain disease states.

Definitions

Unless defined otherwise, technical and scientific terms used in this application have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described. As used in this application, except as otherwise expressly provided herein, each of the following terms shall have the meaning set forth below.

As used herein, "renal cortical neoplasm" when used in singular or plural, shall mean a tumor that arises from the cells of the renal parenchyma, the tissue (comprised of cells) that constitutes the essential or functional part of the kidney versus the associated connective or supporting tissues. A renal cortical neoplasm is classified according to the cell type of origin (epithelial, mesenchymal, or embryonic) and biologic behavior (benign or malignant). It is further classified according to the appearance of the cells (cytoplasm and growth pattern) and genetic abnormalities. In the current application, the term renal cortical neoplasm refers to those with an epithelial cell of origin.

As used herein, "tumor" shall refer to all neoplastic cell growth and proliferation, whether malignant or benign, and all pre-cancerous and cancerous cells and tissues.

As used herein, the terms "cancer" and "cancerous" refer to or describe the physiological condition in mammals that is typically characterized by unregulated cell growth. Examples of cancer include, but are not limited to, renal cancer, breast cancer, ovarian cancer, colon cancer, lung cancer, prostate cancer, hepatocellular cancer, gastric cancer, pancreatic cancer, cervical cancer, liver cancer, bladder cancer, cancer of the urinary tract, thyroid cancer, carcinoma, melanoma, and brain cancer.

As used herein, a "renal mass" when used in singular or plural shall refer to a biological entity (cells, liquid, tissue) associated with the kidney and surrounding structures.

As used herein, "renal cell carcinoma" shall refer to a malignant subtype of a renal cortical neoplasm that arises in epithelial cells.

As used herein, "morphologic analysis" shall mean microscopic examination of tissues (unstained or stained with dyes and/or antibodies) with the intent to define the tissue type based on cell appearance, cell structure, overall patterns of cell organization, and staining intensity and pattern.

As used herein, "biopsy specimen" shall mean a biological sample of tissue, cells, or liquid taken from the human body.

As used herein, a "marker", "cellular marker", "molecular marker", or "disease marker" is any molecular structure or substructure that is correlated with a disease state or pathogen. Broadly defined, a marker is a biological indicator that may be deliberately used by an observer or instrument to reveal, detect, or measure the presence or frequency and/or amount of a specific condition, event or substance. For example, molecular markers are specific molecules, such as proteins or protein fragments, whose presence within a cell or tissue indicates a particular disease state.

As used herein, a "label" may be any substance that can be attached to a probe so that when the probe binds to the marker a signal is emitted or the labeled probe can be detected by a human observer or an analytical instrument. Labels envisioned by the present invention are any labels that emit a signal and allow for identification of a component in a sample. Although a fluorescent label is preferred, the invention is in no way limited to use of a fluorescent label. Other labels include radioactive, chromogenic or enzymatic moieties. Therefore, possible methods of detection include, but are not limited to, fluorescent in situ hybridization, in situ hybridization, immunocytochemistry, immunohistochemistry, flow cytometry and image cytometry.

As used herein, the term "reader instrumentation" refers to the analytical equipment used to detect a probe.

As used herein, a "probe" is any molecular structure or substructure that binds to a disease marker. Molecular probes are homing devices used by biologists and clinicians to detect and locate markers indicative of the specific disease states.

As used herein, "BAC" (Bacterial artificial chromosome) is a laboratory creation involving an artificially constructed chromosome in which medium-sized segments of DNA (100,000 to 300,000 bases in length) that come from another species are cloned into bacteria. Once the foreign DNA has been cloned into the bacteria's chromosome, many copies of it can be made (amplified) and sequenced. Bacterial artificial chromosome is abbreviated BAC.

As used herein, "probe panel" shall mean a group of defined probes.

As used herein, "histologic subtype" shall mean a subgroup of a major tissue or cell type categorized according to differential morphologic aspects of the tissue or cells. Histologic subtypes have previously been defined by morphologic analysis for the subgroups of a major type.

As used herein, a "genomic region" shall mean a length of DNA contained within the human genome complement with location defined with respect to either the chromosomal band or nucleotide position in the human genome.

As used herein, "cytogenetic abnormality" when used in singular or plural, shall mean an alteration in the human genome that can be detected by examination of the chromosomes.

As used herein, "cytogenetic assay" shall mean a laboratory assay that examines chromosomes.

As used herein, "clear cell renal cell carcinoma" (ccRCC) shall mean a histologic subtype of renal cortical neoplasm that is malignant. Histologically, it is characterized by tumor cells with clear cytoplasm and an acinar growth pattern. At the chromosomal level, they typically show loss of 3p, 3q, 9p21, 14q22 and 5q.

As used herein, "papillary renal cell carcinoma" (pRCC) shall mean a histologic subtype of renal cortical neoplasm that is malignant. It is histologically characterized by a papillary growth pattern, where the cytoplasm of individual cells may be basophilic, eosinophilic or partially clear. At the chromosomal level, pRCCs typically show gain of chr 7 and 17 and loss of Y.

As used herein, "chromophobe renal cell carcinoma" (chRCC) shall mean a histologic subtype of renal cortical neoplasm that is malignant. Chromophobe renal cell carcinomas are characterized by large polygonal cells with prominent cell membranes arranged in a cobblestone pattern. At the chromosomal level, chRCCs typically shows loss of chrs 1, 2, 6, 10, 13, 17 and 21.

As used herein, "oncocytoma" (OC) shall mean a histologic subtype of renal cortical neoplasm that is benign. Oncocytomas are composed of large epithelial cells called oncocytes, which have abundant eosinophilic homogeneous or granular cytoplasm and uniform small nuclei. The oncocytes are arranged in nests, cords, or tubules. At the chromosomal level, OCs typically show loss of 1p, 14q and Y. OCs also show translocation at 11q13.

Embodiments

This invention provides a panel for detecting the type of renal cortical neoplasm present in a sample, wherein said panel comprises a plurality of probes each of which is individually capable of hybridizing selectively to a specific marker or a correlate thereof associated with a chromosomal abnormality diagnostic or indicative of the type of renal cortical neoplasm.

In one embodiment of the instant invention, said sample is a renal biopsy sample.

In another embodiment of the instant invention, said plurality of probes comprises at least one probe individually capable of hybridizing selectively to the marker identified as D3S4208 or a correlate thereof at 3p21, or VHL or a correlate thereof at 3p25, or D3S3634 or a correlate thereof at 3q11, or D5S1469 or a correlate thereof at 5q33, or D5S2095 or a correlate thereof at 5p13, or 7 α-satellite or a correlate thereof at 7 centromere, or D17S651 or a correlate thereof at 17q21, or D3S1212 or a correlate thereof at 3q26, or D6S1941 or a correlate thereof at 2p23, or D10S1765 or a correlate thereof at 10q23, or D6S2419 or a correlate thereof at 6p22, or D1S2471 or a correlate thereof at 1q23, or D14S1007 or a correlate thereof at 14q32, or Y satellite III or a correlate thereof at Yq12, or 5'TFE3 or a correlate thereof at a genomic locus point centromeric to Xp11, or 3'TFE3 or a correlate thereof at a genomic locus point telomeric to Xp11, or 5'CCND1 or a correlate thereof at a genomic locus point centromeric to 11q13, or 3'CCND1 or a correlate thereof at a genomic locus point telomeric to 11q13.

In yet another embodiment of the instant invention, said plurality of probes comprises at least one probe individually capable of hybridizing selectively to any single marker identified along the q arm of chromosome 3 or the p or q arms of chromosome 5 or any single marker identified along chromosomes 1, 2, 6, 7, 10, 14, 17 or Y.

This invention further provides a method for detecting the subtype of renal cortical neoplasm present in a sample, the method comprising: (a) a panel comprising a plurality of probes each of which is individually capable of hybridizing selectively to a specific marker or a correlate thereof associated with a chromosomal abnormality diagnostic or indicative of the subtype of renal cortical neoplasm; (b) hybridizing said sample with said plurality of probes; (c) analyzing the hybridization pattern of each of the said probes to said specific markers or correlates thereof after said hybridization, in order to detect the presence or absence of one or more chromosomal abnormalities associated with a subtype of renal cortical neoplasm; and (d) if one or more chromosomal abnormalities are detected within said sample, classifying the subtype of renal cortical neoplasm present according to the diagnosis matrix shown in FIG. 4.

In one embodiment of the instant method, said sample is a renal biopsy sample.

In a further embodiment of the instant method, step (c) is performed by fluorescence in situ hybridization (FISH).

In another embodiment of the instant method, said panel comprises at least one probe individually capable of hybridizing to 5'TFE3 or a correlate marker thereof at a genomic locus point centromeric to Xp11 and at least one probe individually capable of hybridizing to the 3'TFE3 or a correlate marker thereof at a genomic locus point telomeric to Xp11, wherein detection of the translocation of Xp11 after said hybridization, is diagnostic for Xp11-associated RCC.

In yet another embodiment of the instant method, said panel comprises at least one probe individually capable of hybridizing to D3S4208 or a correlate marker thereof at the genomic locus point 3p21 and at least one probe individually capable of hybridizing to VHL or a correlate marker thereof at the genomic locus point 3p25, wherein detection of the loss of 3p21 or 3p25 or both after said hybridization, is diagnostic for clear cell renal cell carcinoma (ccRCC).

In yet another embodiment of the instant method, said panel comprises at least one probe individually capable of hybridizing to D3S3634 or a correlate marker thereof at 3q11 or any single genomic locus point along the q arm of chromosome 3, wherein detection of the loss of the q arm of chromosome 3 after said hybridization, is indicative of ccRCC.

In yet another embodiment of the instant method, said panel comprises at least one probe individually capable of hybridizing to D5S2095 or a correlate marker thereof at 5p13 or any single genomic locus point along the p arm of chromosome 5 wherein detection of the gain of the p arm of chromosome 5 after said hybridization, is indicative of ccRCC.

In yet another embodiment of the instant method, said panel comprises at least one probe individually capable of hybridizing to D5S1469 or a correlate marker thereof at 5q33 or any single genomic locus point along the q arm of chromosome 5 wherein detection of the gain of the q arm of chromosome 5 after said hybridization, is indicative of ccRCC.

In yet another embodiment of the instant method, said panel comprises at least one probe individually capable of hybridizing to D14S1007 or a correlate marker thereof at 14q32 or any single genomic locus point along chromosome 14, wherein detection of the loss of chromosome 14 after said hybridization, is indicative of ccRCC.

In yet another embodiment of the instant method, said panel comprises at least one probe individually capable of hybridizing to Y satellite III or a correlate marker thereof at Yq12 or any single genomic locus point along chromosome Y wherein detection of the loss of chromosome Y after said hybridization, is indicative of ccRCC.

In yet another embodiment of the instant method, said panel comprises at least one probe individually capable of hybridizing to 7 α-satellite or a correlate marker thereof at 7 centromere or any single genomic locus point along chromosome 7 and at least one probe individually capable of hybridizing to D17S651 or a correlate marker thereof at 17q21 or any single genomic locus point along chromosome 17, wherein detection of the gain of chromosome 7 or chromosome 17 or both after said hybridization, is diagnostic for papillary renal cell carcinoma (pRCC).

In yet another embodiment of the instant method, said panel comprises at least one probe individually capable of hybridizing to D3S1212 or a correlate marker thereof at 3q26 or any single genomic locus point along the q arm of chromosome 3, wherein detection of the gain of the q arm of chromosome 3 after said hybridization, is indicative of pRCC.

In yet another embodiment of the instant method, said panel further comprises at least one probe individually capable of hybridizing to Y satellite III or a correlate marker thereof at Yq12 or any single genomic locus point along chromosome Y, wherein detection of the loss of chromosome Y after said hybridization, is indicative of pRCC.

In yet another embodiment of the instant method, said panel comprises at least one probe individually capable of hybridizing to D6S1941 or a correlate marker thereof at 2p23 or any single genomic locus point along chromosome 2, at least one probe individually capable of hybridizing to D6S2419 or a correlate marker thereof at 6p22 or any single genomic locus point along chromosome 6, at least one probe individually capable of hybridizing to D10S1765 or a correlate marker thereof at 10q23 or any single genomic locus point along chromosome 10, and at least one probe individually capable of hybridzing to D17S651 or a correlate marker thereof at 17q21 or any single genomic locus point along chromosome 17, wherein detection of the loss of two or more of the said chromosomes after said hybridization, is diagnostic for chromophobe renal cell carcinoma (chRCC).

In yet another embodiment of the instant method, said panel comprises at least one probe individually capable of hybridizing to D1S2471 or a correlate marker thereof at 1q23 or any single genomic locus point along chromosome 1, wherein detection of the loss of chromosome 1 after said hybridization, is indicative of chRCC.

In yet another embodiment of the instant method, said panel comprises at least one probe individually capable of hybridizing to Y satellite III or a correlate marker thereof at Yq12 or any single genomic locus point along chromosome Y, wherein detection of the loss of chromosome Y after said hybridization, is indicative of chRCC.

In yet another embodiment of the instant method, said panel comprises at least one probe individually capable of hybridizing to D1S2471 or a correlate marker thereof at 1q23 or any single genomic locus point along chromosome 1, at least one probe individually capable of hybridizing to D14S1007 or a correlate marker thereof at 14q32 or any single genomic locus point along chromosome 14, and at least one probe individually capable of hybridizing to Y satellite III or a correlate marker thereof at Yq12 or any single genomic locus point along chromosome Y, wherein detection of the loss of one or more of said chromosomes after said hybridization, is diagnostic for oncocytoma (OC).

Finally, in a further embodiment of the instant method, said panel comprises at least one probe individually capable of hybridizing to 5'CCND1 or a correlate marker thereof at a genomic locus point centromeric to 11q13 and at least one probe individually capable of hybridizing to 3'CCND1 or a correlate marker thereof at a genomic locus point telomeric to 11q13, wherein detection of the translocation of 11q13 after said hybridization, is diagnostic for OC.

This invention is illustrated in the Experimental Details section which follows. This section is set forth to aid in an understanding of the invention but is not intended to, and should not be construed to, limit in any way the invention as set forth in the claims which follow thereafter.

Experimental Details

Discussion

As previously noted, the present invention utilizes probes for detecting specific chromosomal abnormalities associated with specific subtypes of renal cortical neoplasms.

A probe is any molecular structure or substructure that binds to a disease marker. Molecular probes, such as the ones of the present invention, may best be described as homing devices used by biologists and clinicians to detect and locate markers indicative of the specific disease state, here, the detection of the type of renal cortical neoplasm present in a sample.

As with other types of probes, the probes of the present invention contain a label. The label may be any substance that can be attached. A probe containing a label is often referred to herein as a "labeled probe". The label may be any substance that can be attached to any probe so that when the probe binds to the marker a signal is emitted or the labeled probe can be detected by a human observer or an analytical instrument. This label may also be referred to as a "tag". The label may be visualized using reader instrumentation. The term "reader instrumentation" refers to the analytical equipment used to detect a probe.

Labels envisioned by the present invention are any labels that emit a signal and allow for identification of a component in a sample. Preferred labels include radioactive, fluorogenic, chromogenic or enzymatic moieties. Therefore, possible methods of detection include, but are not limited to, immunocytochemistry, immunohistochemistry, in situ hybridization, fluorescent in situ hybridization (FISH), flow cytometry and image cytometry. The signal generated by the labeled probe is of sufficient intensity to permit detection by a medical practitioner.

As discussed in the "Definition" section above, a marker is any molecular structure or sub-structure that is correlated with a disease state, again, here, the type of renal cortical neoplasm present in a sample. Broadly defined, a marker is a biological indication that may be deliberately used by an observer or instrument to reneal, detect or measure the presence or frequency or amount of a specific condition. Here, applicants have identified markers associated with subtypes of renal cortical neoplasms. However, the individual markers themselves are mere tools of the present invention. Therefore, the invention is not limited to specific markers. Suitable markers of the present invention include, but are not limited to, those listed in FIGS. 2 and 3.

The Panel

Based on a literature survey of cytogenetic and molecular cytogenetic applications in the study of RCC, the applicants identified a group of genomic regions whose respective gain/loss/rearrangement would distinguish the most common histologic subtypes of RCC. Together, these subtypes comprise upwards of 90% of renal cortical neoplasms. The probes were designed taking into account the single abnormalities that define a subtype (exemplified by 3p loss in ccRCC) along with secondary associated abnormalities (exemplified by chr5 gain and 14q loss in ccRCC), as well as the complex abnormalities that together define a subtype (exemplified by chr7 and chr17 gain in pRCC, and by chr2, chr6, chr10, and chr17 loss in chRCC).

Specifically, rearrangement of the TFE3 gene as detected by FISH using a probe centromeric to the breakpoint of the rearrangement and telomeric to the breakpoint of the rearrangement, is an abnormality that permits classification of the sample as an Xp11 translocation-associated RCC.

The loss of the 3p21 and/or the 3p25 genomic regions as detected by FISH using a probe that maps to 3p21 and a probe that maps to 3p25 are abnormalities that permit classification of the sample as a ccRCC.

The loss of 3q and/or gain of chr5 as detected by FISH using a probe that maps to 3q11, a probe that maps to 5q33, and a probe that maps to 5p13 are abnormalities highly associated with ccRCC and can be used in the classification of ccRCC. One of ordinary skill in the art would readily understand that the 3q11, 5q33, and 5p13 probes each represent only one of many probes that could suffice for the detection of the abnormality of the involved regions of 3q or chromosome 5.

The loss of chromosome 14 and/or the Y chromosome as detected by FISH using a probe that maps to 14q32 and a probe that maps to Yq12 are abnormalities that are associated with ccRCC but do not alone permit classification of the sample as ccRCC. One of ordinary skill in the art would readily understand that the 14q32, and Yq12 probes each represent only one of many probes that could suffice for the detection of the abnormality of the involved regions of chr14, and Y.

The gain of chromosome 7 and/or of chromosome 17 as detected by FISH using a probe that maps to 7 centromere and a probe that maps to 17q21 are abnormalities that permit classification of the sample as pRCC. One of ordinary skill in the art would readily understand that the 7 centromere and 17q21 probes each represent only one of many probes that could suffice for the detection of the abnormality of the involved regions of chromosome 7 and chromosome 17.

The gain of 3q as detected by FISH using a probe that maps to 3q26 is an abnormality highly associated with pRCC but alone cannot be used in the classification of pRCC. One of ordinary skill in the art would readily understand that the 3q26 probe represents only one of many probes that could suffice for the detection of the abnormality of the involved region of 3q.

The loss of chromosome 2, chromosome 6, chromosome 10, or chromosome 17 as detected by FISH using a probe that maps to 2p23, a probe that maps to 6p22, a probe that maps to 10q23, and a probe that maps to 17q21 are abnormalities, often in various combinations, highly associated with chRCC and can be used in the classification of ccRCC. One of ordinary skill in the art would readily understand that the 2p23, 6p22, 10q23, and 17q21 probes each represent only one of many probes that could suffice for the detection of the abnormality of the involved regions of chromosome 2, chromosome 6, chromosome 10, and chromosome 17.

The loss of chromosome 1, chromosome 14, and/or the Y chromosome as detected by FISH using a probe that maps to 1q23, a probe that maps to 14q32, and a probe that maps to Yq12 are abnormalities that permit classification of the sample as OC. One of ordinary skill in the art would readily understand that the 1q23, 14q32, and Yq12 probes each represent only one of many probes that could suffice for the detection of the abnormality of the involved regions of chromosome 1, chromosome 14, and the Y chromosome.

The rearrangement of the CCND1 gene as detected by FISH using a probe centromeric to the breakpoint of the rearrangement and telomeric to the breakpoint of the rearrangement, is an abnormality that permits classification of the sample as OC.

Finally, once the informative genomic regions and the associated abnormalities were identified, specific markers were identified that mapped to the respective regions using the UCSC Genome Browser of the human genome sequence NCBI Build 36.1.

Next, BAC-based probes were selected based on genome position (cover marker regions), lack of noted chimerism, and relative content of repeat sequences. FIG. 2 lists the genomic regions and the respective markers selected for each region of interest. Thus, each sample is submitted a total of nineteen (19) hybridizations, one for each probe. Also listed in FIG. 2 are the respective fluorescent signals expected from differential fluorescent labeling.

The BAC-based probes for the total of 19 markers were grown and fluorescently labeled using routine labeling methods used by one of ordinary skill in the art. The fluorochromes used were SPECTRUMRED [trade] (red fluorochrome), SPECTRUMGREEN [trade] (green fluorochrome), and diethylaminocoumarine (DEAC) (blue fluorochrome). For each probe, the size of the respective labeled product was confirmed and if needed, optimized in an additional labeling reaction.

Additionally, as a control for assessment of ploidy, a probe was designed that mapped to the genomic locus point 22q11, as it showed little involvement in renal cortical neoplasms based on a literature survey.

Interphase Fluorescent in Situ Hybridization (FISH)

As commonly understood, FISH is a molecular cytogenetic method wherein a single-stranded fluorescent-labeled nucleic acid sequence (probe) complementary to a target genomic sequence is hybridized to metaphase chromosomes and interphase nuclei to detect the presence or absence of a given abnormality (28, 29). The major advantage of FISH is that it can be applied to non-dividing (interphase) cells and to a variety of specimen types.

Depending on the color scheme and placement of the probes (spanning or flanking the genomic region of interest), interpretation of hybridized nuclei preparations can involve counting of hybridization signals per nucleus (genomic gain/loss), identification of fusion hybridization signals (rearrangement), or identification of signals that break apart (rearrangement). In a clinical laboratory setting, FISH is considered an adjunct to traditional G-banding metaphase chromosome analysis. The impact of FISH-based assays on patient management is well established for a broad range of cancers for both diagnostic and prognostic purposes (28).

Although, FISH is the method of choice in the present invention, one of ordinary skill in the art would understand that other methods could be employed as well. And the methodology of the present invention is in no way limited to FISH.

The chromosomal abnormalities associated with the histologic subtypes of RCC listed in FIG. 1 have been either confirmed/identified/reassessed by FISH with probes mapped to the respective regions (11, 30-34).

Probes used in FISH are generally pieces of human genomic DNA of high complexity (upwards of 40 kbp) that contain both unique sequences and repetitive sequences. Due to the presence of the repeat sequences, Cot-1 DNA is necessary in the hybridization to the human specimen to suppress non-specific fluorescent signal leaving, predominantly that signal due to hybridization of the unique portions of the probe.

Use of FISH

As in the routine development of any probe to be utilized in a clinical FISH-based assay, labeled probes were initially hybridized to normal peripheral blood lymphocyte preparations that included both interphase and metaphase cells. This is three-fold in purpose: (i) to confirm the expected chromosome hybridization localization, (ii) to rule out chimerism, and, (iii) to establish the cut-offs for the presence or absence of the chromosomal abnormality being detected. FIG. 3 lists each of the markers and the respective results obtained upon hybridization to normal lymphocytes for validation of the probes.

All the high complexity BAC-based probes tested were found to be non-chimeric and to hybridize to the correct location on reverse-DAPI-stained metaphase chromosomes. Also listed are the signal pattern cut-offs (mean plus three standard deviations), above which for probes used in copy number evaluation would be considered to have an altered copy number. The four (4) translocation probes (11q13 and Xp11) were designed as "break apart" probe sets such that upon translocation the individual probe signals would be evident (red and green) rather than a normal merged "yellow" signal. As outlined in the application, normal pattern cut-offs were established using the sample type to be used in the assay. Here, applicants' used biopsies of morphologically normal kidney.

Following this initial routine work-up of the high complexity probes for use in a FISH-based methodology, we obtained ten renal mass needle biopsies. These biopsies comprised part of a larger cohort of 145 biopsies obtained from nephrectomy (partial or total) specimens consecutively accessioned in the Department of Pathology, Memorial Sloan-Kettering Cancer Center. In that IRB-approved study, the morphology-based histologic subtype of each core biopsy was compared with that obtained for the specimen proper.

For the preliminary FISH analysis, ten needle biopsies were selected and were submitted to FISH analysis for all probe set combinations. The respective morphology-defined histologic subtype was blinded until after a FISH-defined histologic subtype was assigned to each specimen.

In brief, the fixed cell sections were pretreated with pepsin, washed in PBS, and then dehydrated in an ethanol series. The probes were hybridized in the presence of Cot-1 DNA to the sections and followed by a series of salt/detergent-containing washes. Nuclei were counterstained with DAPI. Of note, scoring was possible in all of the cases and called positive for the abnormality if the percentage of nuclei showing the abnormality was above the cut-off (FIG. 3).

In order to classify the specimens based on the loss/gain/rearrangement of the genomic sites, a decision tree or diagnosis matrix was developed as shown in FIG. 4. In accordance with the diagnosis matrix, the genetic abnormalities, as detected by FISH for each of the samples, were interpreted and a FISH-defined subtype assigned (FIG. 4).

Methods: Biopsies and Specimens

Sections of 145 needle biopsies were available for analysis. The biopsies were obtained from kidney masses resected from patients undergoing treatment at Memorial Sloan Kettering Cancer Center (MSKCC). Two needle biopsies were retrieved from each resected specimen using 18-gauge needles, and immediately fixed in 10% formalin. Hematoxylin and eosin slides were prepared from cores and resected specimens. Histopathologic examination of the cores was performed blinded to the final diagnosis of the excised specimen. The tumors were classified according to the World Health Organization (WHO) system (2004) (FIG. 1) and the histology compared between the biopsy and the respective resected specimen. Of note, 18% of all core biopsies were considered non-diagnostic for several reasons, the most prevalent being limitations of obtaining adequate material for diagnosis from small masses. Of the 119 cores for which histologic examination was diagnostic, 92% concordance was evident between that of the core and the resected specimen (sensitivity). The highest was observed for ccRCC (97%) and the lowest for chRCC (62%). A differential diagnosis could not be ruled out for six cores (particularly prevalent for chRCC), and for three, a discordant subtype was diagnosed. One core was RCC but could not be further classified. Since no malignant biopsy was a false positive, then the specificity and positive predictive value of diagnosis by histologic examination of this cohort is 100%. Of the six readable benign OC, two were classified as malignant. Therefore, the negative predictive value is 67%.

At least two needle biopsies from coded histopathologically normal or unaffected kidneys were made available for assay with the entire probe panel to establish cut-offs for the absence/presence of an abnormality.

When necessary, nuclei from sections of the resected sample specimen were isolated and prepared for hybridization using FISH. Methodology is in place for performance of this modified assay according to Visakorpi et al (40). Briefly, 30 micron paraffin sections will be dewaxed in xylene at room temperature, rehydrated with 95%, 75%, and 50% ethanol, and enucleated with subtilisin Carlsberg (0.1% protease XXIV, 0.1 M Tris, 0.07 M NaCl, pH 7.2). Pelleted nuclei will be washed twice with phosphate-buffered saline without Ca/Mg (PBS) and fixed by resuspending the nuclei pellet in freshly prepared fixative (acetic acid/methanol [3:1]). Fixed nuclei suspensions can be stored at −20° C. prior to preparation of slides.

Probe Preparation and Labeling

In preparation of the BAC-based probes used in the present invention, the 500 ng of the respective BAC DNA is labeled by nick translation using conventional methods with the respective fluorochrome. For BAC probes, labeling is performed for 16 hours and for plasmid probes, for 6 hours. An aliquot is checked by gel electrophoresis to ensure that the size of the labeled fragments are 100-300 bp. Cot-1 DNA and human placental DNA are added prior to ethanol precipitation with 0.3M NaOAc. The pellet is resuspended in 12 µl distilled water. For multi-color hybridizations, 500 ng of each probe is labeled and then co-precipitated. For each hybridization, 3 µl of the labeled probe is combined with 7 µl of hybridization mix (60% formamide, 10% dextran sulphate, 0.2% SDS, 2× SSC).

Sample Specimen Preparation and Hybridization

The renal biopsies were received as fixed cell sections attached to glass slides, blinded with respect to pathology. Routinely, two probe sets per section are hybridized to one slide. To remove interfering stain, slides are rinsed in acetic acid/methanol (3:1) for 10 minutes at room temperature and dehydrated in a series of ethanol washes (70%, 80%, and 100%) (1 minute each at room temperature). Slides are then pretreated with pepsin (0.004% in 0.01N HCl) at 37° C. for 5-10 minutes, washed twice in PBS at room temperature for 5 minutes each, dehydrated in an ethanol series (70% and 100%) for 2 minutes each at room temperature, and air-dried. The respective probe set in the hybridization mix is applied to the target area of the slide, cover-slipped, and sealed with rubber cement. The amount of probe/hybridization mix depends on the area of hybridization: 5 µl per 18 mm² area and 10 µl per 22 mm² area. The probe/hybridization mix and specimen are co-denatured at 80° C. for 3 minutes and incubated overnight in a humidified chamber at 37° C. After removal of the rubber cement and the coverslip, the slide is submitted to a series of washes: once in 2× SSC (room temperature for 5 minutes), twice in 2× SSC plus 0.1% Tween-20 (45° C. for 3 minutes), twice in 0.5× SSC plus 0.1% SDS (45° C. for 5 minutes), twice in distilled water (briefly at room temperature). The slides are air-dried, DAPI counterstain applied, and slides are cover-slipped. The slides are kept in a light-sensitive box until scoring is performed.

Signal Screening and Subtype Determination

The hybridized biopsy sample/slide is scored using an epi-fluorescence microscope equipped with a DAPI single pass filter (to view DAPI and blue hybridization signals), a FITC single pass filter (to view green hybridization signals), a Rhodamine single pass filter (to view red hybridization signals), a CCD camera, and operated using Isis Imaging Software (Metasystems). The slide is first examined for cell density, background, nuclear morphology, and hybridization signal strength. Using established criteria (derived from experience in performing FISH with other probes on clinical sample specimens), the quality of hybridization is ranked and if suitable for analysis, scored.

For scoring, 200-300 nuclei are consecutively scored with no discrimination of cells scored based on cell morphology. The nuclei are scored according to the signal patterns obtained for each probe set, with each type of pattern noted in the count. For all probe sets, except the translocation-detecting sets (11q13 and Xp11), the expected normal pattern would be two signals of each color. For the 11q13 and Xp11 probe sets, two fusion signals are normally expected. Scores are recorded and the percentage of cells with an abnormal pattern reflecting the respective abnormality are calculated, and interpreted according to the ploidy, established by the copy number of chromosome 22. Additionally, in most cases the ploidy is also reflected by uninvolved chromosomes for a specific subtype.

Finally, using the decision tree in FIG. 4, the subtype of the biopsy sample is determined.

Statistical Comparison of FISH-Based Subtype and Morphology-Based Subtype

For each case, three histologic subtype classifications were compared: (i) FISH-based of the biopsy sample, (ii) morphology-based of the biopsy sample, and (iii) morphology-based of the sample specimen proper.

For the subtype determined using the FISH-based assay, there are six possible classifications: ccRCC, pRCC, chRCC, OC, Xp11-associated, and "non-diagnostic". The non-diagnostic cases comprise those cases for which no chromosomal abnormalities were detected that are consistent with one of the five subtypes or for which the FISH-based assay could not be performed for technical reasons.

For the subtype determined by morphology (biopsy sample and sample specimen proper), the same six classifications are possible, but in this case, the non-diagnostic group comprised, in the case of the biopsy, those diagnosed as RCC-Un (5 biopsies), other neoplasm (11 biopsies), or non-diagnostic for technical reasons (26 biopsies); and in the case of the specimen proper, those diagnosed as RCC-Un (4 biopsies) and other neoplasm (11 biopsies).

Sensitivity and specificity was calculated for subtype classifications based on: (i) FISH-based subtype of the biopsy sample versus morphology-based subtype of the biopsy sample, (ii) FISH-based subtype of the biopsy sample versus the morphology-based subtype of the specimen sample proper, (iii) morphology-based subtype of the biopsy sample versus morphology-based subtype of the sample specimen proper, and (iv) combined FISH- and morphology-based subtype of the biopsy versus morphology-based subtype of the resected specimen. In the last comparison (v), if the biopsy subtypes (FISH-versus morphology-based) were discordant then both alternatives were analyzed: one where all discordant FISH-based subtypes would be used for comparison and one where all discordant morphology subtypes would be used. Where only one of the two biopsy subtypes was diagnostic, then that subtype was used for the comparison.

Positive and negative predictive values were also calculated and evaluated in a similar manner. The preliminary studies indicated that sensitivity and specificity in the present invention to be above 0.70. All diagnostic measures are reported with exact 95% confidence intervals. Table 1 provides 95% exact confidence intervals for a sample size of 145 for a range of proportions.

TABLE 1

95% Exact Confidence Intervals (CI) for a Sample Size of 145.

| Proportion | 95% Exact CI |
| --- | --- |
| 0.70 | (0.62, 0.78) |
| 0.75 | (0.67, 0.82) |
| 0.80 | (0.73, 0.87) |
| 0.85 | (0.78, 0.90) |
| 0.95 | (0.90, 0.98) |
| 0.97 | (0.92, 0.99) |

Rationale

In the present invention, a panel of BAC-based probes have been evaluated for the ability to successfully distinguish the four main histologic subtypes of renal cortical neoplasms in renal mass biopsies.

As for any FISH-based assay to be used for a clinical purpose, several criteria were first satisfied including: (i) confirmation of hybridization to the correct chromosomal location, (ii) confirmation that the sequence of the probe is as intended, (iii) establishment of cut-offs for the abnormal signal pattern in normal cells of the intended tissue type, and (iv) validation of the probe set in split specimens when possible. The first criterion was established during the testing phase of the probe sets as described above. The second was accomplished by sequence analysis of the respective probes. The third criterion was established using both normal lymphocytes as in the Preliminary Studies and in at least two normal kidney needle biopsy sample specimens, such that biopsies with levels of abnormal signal patterns above the cut-offs (plus three standard deviations from the mean) were called positive for that abnormality.

REFERENCES

1. Jemal A, Siegel R, Ward E, Murray T. Xu J, Thun M J. Cancer statistics, 2007. CA Cancer J Clin 2007; 57(1):43-66.
2. Reuter V E. The pathology of renal epithelial neoplasms. Semin Oncol 2006; 33(5):534-43.
3. Kovacs G. Molecular cytogenetics of renal cell tumors. Adv Cancer Res 1993; 62:89-124.
4. Speicher M R, Schoell B, du Manoir S, et al. Specific loss of chromosomes 1, 2, 6, 10, 13, 17, and 21 in is chromophobe renal cell carcinomas revealed by comparative genomic hybridization. Am J Pathol 1994; 145(2):356-64.
5. van den Berg A, Buys C H. Involvement of multiple loci on chromosome 3 in renal cell cancer development. Genes Chromosomes Cancer 1997; 19(2):59-76.
6. van den Berg E, Dijkhuizen T, Oosterhuis J W, Geurts van Kessel A, de Jong B, Storkel S. Cytogenetic classification of renal cell cancer. Cancer Genet Cytogenet 1997; 95(1): 103-7.
7. Wilhelm M, Veltman J A, Olshen A B, et al. Array-based comparative genomic hybridization for the differential diagnosis of renal cell cancer. Cancer Res 2002; 62(4):957-60.
8. Perot C, Boccon-Gibod L, Bouvier R, et al. Five new cases of juvenile renal cell carcinoma with translocations involving Xp11.2: a cytogenetic and morphologic study. Cancer Genet Cytogenet 2003; 143(2):93-9.
9. Hoglund M, Gisselsson D, Soller M, Hansen G B, Elfving P, Mitelman F. Dissecting karyotypic patterns in renal cell carcinoma: an analysis of the accumulated cytogenetic data. Cancer Genet Cytogenet 2004; 153(1):1-9.
10. Fuzesi L, Frank D, Nguyen C, Ringert R H, Bartels H, Gunawan B. Losses of 1p and chromosome 14 in renal oncocytomas. Cancer Genet Cytogenet 2005; 160(2): 120-5.
11. Paner G P, Lindgren V, Jacobson K, et al. High incidence of chromosome 1 abnormalities in a series of 27 renal oncocytomas: cytogenetic and fluorescence in situ hybridization studies. Arch Pathol Lab Med 2007; 131(1):81-5.
12. Banks R E, Tirukonda P, Taylor C, et al. Genetic and epigenetic analysis of von Hippel-Lindau (VHL) gene alterations and relationship with clinical variables in sporadic renal cancer. Cancer Res 2006; 66(4):2000-11.
13. Kaelin W G, Jr. The von Hippel-Lindau tumor suppressor protein and clear cell renal carcinoma. Clin Cancer Res 2007; 13(2 Pt 2):680s-4s.
14. Shuch B M, Lam J S, Beildegrun A S, Figlin R A. Prognostic factors in renal cell carcinoma. Semin Oncol 2006; 33(5):563-75.
15. Knight D A, Stadler W M. Prognostic factors in localized renal cell cancer. BJU Int 2007; 99(5 Pt B):1212-6.
16. Lam J S, Breda A, Belldegrun A S, Figlin R A. Evolving principles of surgical management and prognostic factors for outcome in renal cell carcinoma. J Clin Oncol 2006; 24(35):5565-75.
17. Leibovich B C, Blute M L. Surgical management of renal cell carcinoma. Semin Oncol 2006; 33(5):552-62.
18. Deane L A, Clayman R V. Laparoscopic nephrectomy for renal cell cancer: radical and total. BJU Int 2007; 99(5 Pt B):1251-7.

19. Marberger M. Ablation of renal tumours with extracorporeal high-intensity focused ultrasound. BJU Int 2007; 99(5 Pt B):1273-6.
20. McDougal W S. Radiofrequency ablation of renal cell carcinoma. BJU Int 2007; 99(5 Pt B):1271-2.
21. Stein R J, Kaouk J H. Renal cryotherapy: a detailed review including a 5-year follow-up. BJU Int 2007; 99(5 Pt B):1265-70.
22. Motzer R J, Bukowski R M. Targeted therapy for metastatic renal cell carcinoma. J Clin Oncol 2006; 24(35): 5601-8.
23. Silverman S G, Gan Y U, Mortele K J, Tuncali K, Cibas E S. Renal masses in the adult patient: the role of percutaneous biopsy. Radiology 2006; 240(1):6-22.
24. Crispen P L, Uzzo R G. The natural history of untreated renal masses. BJU Int 2007; 99(5 Pt B):1203-7.
25. Vasudevan A, Davies R J, Shannon B A, Cohen R J. Incidental renal tumours: the frequency of benign lesions and the role of preoperative core biopsy. BJU Int 2006; 97(5):946-9.
26. Maturen K E, Nghiem H V, Caoili E M, Higgins E G, Wolf J S, Jr., Wood D P, Jr. Renal mass core biopsy: accuracy and impact on clinical management. AJR Am J Roentgenol 2007; 188(2):563-70.
27. Remzi M, Katzenbeisser D, Waldert M, et al. Renal tumour size measured radiologically before surgery is an unreliable variable for predicting histopathological features: benign tumours are not necessarily small. BJU Int 2007; 99(5):1002-6.
28. Patel A S, Hawkins A L, Griffin C A. Cytogenetics and cancer. Curr Opin Oncol 2000; 12(1):62-7.
29. Carpenter N J. Molecular cytogenetics. Semin Pediatr Neurol 2001; 8(3):135-46.
30. Hughson M D, Dickman K, Bigler S A, Meloni A M, Sandberg A A. Clear-cell and papillary carcinoma of the kidney: an analysis of chromosome 3, 7, and 17 abnormalities by microsatellite amplification, cytogenetics, and fluorescence in situ hybridization. Cancer Genet Cytogenet 1998; 106(2):93-104.
31. Jones T D, Eble J N, Cheng L. Application of molecular diagnostic techniques to renal epithelial neoplasms. Clin Lab Med 2005; 25(2):279-303.
32. Receveur A O, Couturier J, Molinie V, et al. Characterization of quantitative chromosomal abnormalities in renal cell carcinomas by interphase four-color fluorescence in situ hybridization. Cancer Genet Cytogenet 2005; 158(2):110-8.
33. Sanjmyatav J. Rubtsov N, Starke H, Schubert J, Hindermann W, Junker K. Identification of tumor entities of renal cell carcinoma using interphase fluorescence in situ hybridization. J Urol 2005; 174(2):731-5.
34. Barocas D A, Mathew S, DelPizzo J J, et al. Renal cell carcinoma sub-typing by histopathology and fluorescence in situ hybridization on a needle-biopsy specimen. BJU Tnt 2007; 99(2):290-5.
35. Rogan P K, Cazcarro P M, Knoll J H. Sequence-based design of single-copy genomic DNA probes for fluorescence in situ hybridization. Genome Res 2001; 11(6):1086-94.
36. Knoll J H, Rogan P K. Sequence-based, in situ detection of chromosomal abnormalities at high resolution. Am J Med Genet A 2003; 121(3):245-57.
37. Newkirk H L, Knoll J H, Rogan P K. Distortion of quantitative genomic hybridization by Cot-1 DNA: mitigation of this effect. Nucleic Acids Res 2005; 33(22):e191.
38. Mora J R, Knoll J H, Rogan P K, Getts R C, Wilson G S. Dendrimer FISH detection of single-copy intervals in acute promyelocytic leukemia. Mol Cell Probes 2006; 20(2):114-20.
39. Shah R B, Bakshi N, Hafez K S, Wood D P, Jr., Kunju L P. Image-guided biopsy in the evaluation of renal mass lesions in contemporary urological practice: indications, adequacy, clinical impact, and limitations of the pathological diagnosis. Hum Pathol 2005; 36(12):1309-15.
40. Visakorpi T, Hyytinen E, Kallioniemi A, Isola J, Kallioniemi O P. Sensitive detection of chromosome copy number aberrations in prostate cancer by fluorescence in situ hybridization. Am J Pathol 1994; 145(3):624-30.
41. Hoglund M, Gisselsson D, Hansen G B, Sall T, Mitelman F. Multivariate analysis of chromosomal imbalances in breast cancer delineates cytogenetic pathways and reveals complex relationships among imbalances. Cancer Res 2002; 62(9):2675-80.
42. Hoglund M, Gisselsson D, Hansen G B, Mitelman F. Statistical dissection of cytogenetic patterns in lung cancer reveals multiple modes of karyotypic evolution independent of histological classification. Cancer Genet Cytogenet 2004; 154(2):99-109.
43. Chen W, Houldsworth J, Olshen A B, et al. Array comparative genomic hybridization reveals genomic copy number changes associated with outcome in diffuse large B-cell lymphomas. Blood 2006; 107(6):2477-85.

What is claimed is:

1. A panel for detecting the type of renal cortical neoplasm present in a sample, wherein said panel comprises a plurality of labeled probes each of which is individually capable of hybridizing selectively to a specific marker associated with a chromosomal abnormality diagnostic or indicative of the type of renal cortical neoplasm, and wherein said plurality of labeled probes comprises:

a probe that is capable of hybridizing selectively to, 5'TFE3;
a probe that is capable of selectively hybridizing to 3'TFE3;
a probe that is capable of selectively hybridizing to the marker identified as D3S4208;
a probe that is capable of selectively hybridizing to the marker identified as VHL;
a probe that is capable of selectively hybridizing to the marker identified as D3S3634;
a probe that is capable of selectively hybridizing to 7 α-satellite;
a probe that is capable of selectively hybridizing to the marker identified as D17S651;
a probe that is capable of selectively hybridizing to the marker identified as D3S1212;
a probe that is capable of selectively hybridizing to the marker identified as D6S1941;
a probe that is capable of selectively hybridizing to the marker identified as D6S2419;
a probe that is capable of selectively hybridizing to the marker identified as D10S1765;
a probe that is capable of selectively hybridizing to the marker identified as D1S2471;
a probe that is capable of selectively hybridizing to the marker identified as D14S1007;
a probe that is capable of selectively hybridizing to Y satellite III;
a probe that is capable of selectively hybridizing to 5'CCND1;
a probe that is capable of selectively hybridizing to 3'CCND1;

a probe that is capable of selectively hybridizing to the marker identified as D5S2095;

a probe that is capable of selectively hybridizing to the marker identified as D5S1469; and a control probe that is capable of being used to assess ploidy in the sample;

wherein each of said labeled probes comprises a moiety selected from the group consisting of a radioactive moiety, a fluorogenic moiety, a chromogenic moiety, and an enzymatic moiety.

2. The panel of claim 1, wherein said sample is a renal biopsy sample.

3. The panel of claim 1, wherein said control probe is the marker identified as D22S553.

4. The panel of claim 1, wherein each of said labeled probes comprises a label, said label comprising a substance that can be attached to a probe so that when the probe binds to the marker a signal is emitted or the labeled probe can be detected by a human observer or an analytical instrument.

\* \* \* \* \*